(12) United States Patent
Moore et al.

(10) Patent No.: US 10,470,834 B2
(45) Date of Patent: Nov. 12, 2019

(54) TRANSPORTATION CONTAINER FOR ULTRASOUND TRANSDUCER

(71) Applicant: ACERTARA ACOUSTIC LABORATORIES LLC, Longmont, CO (US)

(72) Inventors: Levi Moore, Longmont, CO (US); Peter Leonhardt, Loveland, CO (US)

(73) Assignee: Acertara Acoustic Laboratories LLC, Longmont, CO (US)

(*) Notice: Subject to any disclaimer, the term of this patent is extended or adjusted under 35 U.S.C. 154(b) by 22 days.

(21) Appl. No.: 15/893,187

(22) Filed: Feb. 9, 2018

(65) Prior Publication Data

US 2019/0247136 A1    Aug. 15, 2019

(51) Int. Cl.
| | |
|---|---|
| *A61B 50/30* | (2016.01) |
| *B65D 25/20* | (2006.01) |
| *B65D 25/10* | (2006.01) |
| *A61B 8/12* | (2006.01) |
| *A61B 8/00* | (2006.01) |
| *B65D 25/54* | (2006.01) |

(52) U.S. Cl.
CPC ............... *A61B 50/30* (2016.02); *A61B 8/12* (2013.01); *A61B 8/4422* (2013.01); *B65D 25/101* (2013.01); *B65D 25/20* (2013.01); *B65D 25/54* (2013.01); *B65D 2525/286* (2013.01)

(58) Field of Classification Search
CPC ........... A61B 1/00; A61B 8/12; A61B 8/4422; A61B 50/30; A61B 50/301; B65D 25/20; B65D 25/54; B65D 25/101; B65D 2525/286
USPC .......................................... 206/363–370, 438
See application file for complete search history.

(56) References Cited

U.S. PATENT DOCUMENTS

| | | | | |
|---|---|---|---|---|
| 5,222,600 A | * | 6/1993 | Stoddard ............ | A61B 50/3001 206/370 |
| 5,469,853 A | * | 11/1995 | Law ..................... | A61B 8/0833 600/463 |
| 6,099,464 A | * | 8/2000 | Shimizu ............. | A61B 1/00075 600/104 |
| 7,900,805 B2 | * | 3/2011 | Shelton, IV .......... | A61B 50/30 206/363 |

* cited by examiner

*Primary Examiner* — Bryon P Gehman
(74) *Attorney, Agent, or Firm* — Holzer Patel Drennan

(57) ABSTRACT

Devices and methods for protecting and transporting medical probes including, but not limited to, ultrasound transducers and more specifically ultrasound transducers designed for transesophageal echocardiography (TEE). A transport apparatus may include a housing for protecting a control housing of a medical probe and an elongate member extending from the housing. The elongate member may be configured to engage the insertion tube of the probe and maintain an arch shape of the insertion tube during transport to prevent damage from over-flexing of the insertion tube.

20 Claims, 13 Drawing Sheets

TRANSPORTATION CONTAINER FOR ULTRASOUND TRANSDUCER

FIELD OF THE INVENTION

This application relates generally to acoustic systems and probes and, more specifically, to methods and apparatuses for transporting acoustic systems including ultrasonic probes and transducers.

BACKGROUND

Acoustic (e.g., ultrasonic) imaging is an important technique that may be used at different acoustic frequencies for varied applications that range from medical imaging to nondestructive testing of structures. The techniques generally rely on the fact that different structures have different acoustic impedances, allowing characterization of structures and their interfaces from information embodied by the different scattering patterns that result.

Transmission of ultrasonic waves from an ultrasound transducer towards a target and receipt of the scattered radiation may be managed by modern acoustic-imaging systems, each of which may take a variety of forms. In medical applications, ultrasound transducers may be used to capture imagery of a patient's internal organs. For instance, a transesophageal echocardiogram (TEE) may use a transducer disposed in a tube that is inserted into a patient's esophagus and positioned near the heart to capture imagery of the heart and surrounding tissues.

SUMMARY

Medical probes such as ultrasound transducers are frequently transported between operating or exam rooms where they are used and a sterilization lab where they are disinfected. Transporting a sterile probe from a sterilization lab to an operating room may expose the probe to pathogens that can infect the patient. Similarly, transporting a used probe from an operating room to a sterilization lab may allow pathogens received from the patient onto the probe to contaminate the hospital environments through which the probe is transported. While apparatuses and methods have previously been developed for transporting medical probes, these prior solutions have inherent shortcomings. For example, pillow case-like apparatuses (sometimes actual pillow cases) are frequently used to transport TEE transducers. Although providing a minimal degree of isolation, some pathogens may be able to traverse through such transport devices. Moreover, TEE transducers often cost thousands or tens of thousands of dollars and are susceptible to damage from impact or over-flexing of the insertion tube (e.g., portion configured for insertion into the patient). In this regard, prior transport devices generally fail to provide adequate protection to prevent costly damage.

The inventors have thus determined that devices, methods, and the like (e.g., utilities) are needed to transport medical probes such as but not limited to TEE transducers in manners that provide a sterility barrier and protect the probes from damage. Furthermore, the inventors have determined that such utilities may include use of a transport apparatus that protects a control housing of the probe from impact and prevents an insertion tube of the probe from being over-flexed (e.g., bent into a tight radius that causes damage). In this regard, a transport apparatus of the present invention may include a protective housing for securing a control housing and a bendable member for securing an insertion tube.

In an aspect, an apparatus for transporting a medical probe (i.e., transport apparatus) may include a housing, an elongate member, and at least one fastening mechanism. A housing may be configured for receipt of a body of the medical probe. As an example, the body may comprise a control housing that contains electrical components for operation of the transducer for which it is desirable to provide shielding or protection. A housing of a transport apparatus may include a window comprising an opening through a portion of the housing. The window may be configured for receipt of the insertion tube. The window may be aligned with a flexible elongate member such that the insertion tube may pass through the window when the medical probe is engaged with the apparatus in the transport configuration. In this regard, the body of the medical probe may be disposed within the housing, the insertion tube may be engaged with the elongate member external to the housing, and a portion of the probe interconnecting the insertion tube to the control housing (which may itself be a portion of the insertion tube or the body) may pass through the window.

In an embodiment, an elongate member may be attached to the housing at a proximal end of the elongate member and may extend away from the housing to a distal end that is opposite the proximal end. The elongate member may have an installation configuration in which the elongate member is configured for receipt of an insertion tube of the medical probe. The elongate member may comprise a biasing component configured to bias the elongate member toward the installation configuration and resist bending of the elongate member. In this regard, the elongate member may be biased toward a straight, linear, or flat configuration. The biasing component may comprise any appropriate means including, but not limited to, semi-rigid fibers interwoven into fabric fibers of the elongate member, the elongate member itself being comprised of a semi-rigid material (e.g., plastic, fiberglass, carbon, rubber, etc.), or at least one semi-rigid pole configured for insertion into a compartment, pocket, or other retention device disposed on the elongate member.

In an embodiment, a transport apparatus may comprise a plurality of fastening mechanisms. In one arrangement, a first fastening mechanism may be attached to the elongate member (e.g., near the distal end) and a second fastening mechanism may be attached to the housing. Interconnection of the first and second fastening mechanisms may maintain at least a portion of the elongate member in an arch-shape when the apparatus is in a transport configuration.

In an embodiment, a transport apparatus may include an insertion tube retainer attached to the elongate member and configured to restrict lateral movement of the insertion tube with respect to a width of the elongate member. In this regard, the insertion tube may be retained in contact with the elongate member over at least a portion of its length. In one arrangement, the insertion tube retainer may comprise at least one hook fastener and at least one corresponding loop fastener extending from opposing sides of the elongate member.

In another embodiment, a transport apparatus may include a sanitary sleeve dispenser disposed on the apparatus. A sanitary sleeve dispenser may be configured to dispense disposable sleeves. The disposable sleeves may be configured to envelop at least a portion of the insertion tube to form a sterility barrier between the insertion tube and the elongate member to prevent cross-contamination. A sanitary sleeve may cover the entirety of an insertion tube or may cover a portion of an insertion tube. For example, a sanitary sleeve may cover at least 6 inches of an insertion tube beginning at a distal end opposite the control housing, may cover at least 12 inches, or may cover at least 24 inches. The sanitary sleeve dispenser may be disposed adjacent the distal end of the elongate member upon a side of the elongate member configured for receipt of the insertion tube. In this regard, the sanitary sleeve dispenser may be readily available immediately prior to engaging the insertion probe with the insertion tube retainer. In another arrangement, a sanitary sleeve dispenser may be disposed on a portion of the housing.

In an embodiment, the housing may comprise a movable portion to provide access to an internal cavity of the housing when the movable portion is in an open configuration. The internal cavity may be sized and shaped for receipt of the body of the medical probe. For example, a foam insert may define a volume corresponding in shape to a control housing comprising the body of the medical probe. The body of the medical probe may be at least partially enveloped within the housing when the movable portion is in a closed configuration.

In an embodiment, the first fastening mechanism may comprise a first snap latch disposed upon the housing and the second fastening mechanism may comprise a corresponding second snap latch disposed adjacent to the distal end of the elongate member. In this regard, the elongate member may be curved into an arch when the first and second fastening mechanisms are engaged with one another.

In another embodiment, the elongate member may have a first radius of curvature when in the transport configuration without the at least one semi-rigid pole. In this regard, the absence of a semi-rigid pole may permit the elongate member to assume a geometry that leaves an insertion tube of a probe susceptible to over-flexing. The at least one semi-rigid pole may comprise a resistance to bending sufficient to maintain the insertion tube in a second radius of curvature larger than the first radius of curvature when the apparatus is in the transport configuration with the at least one semi-rigid pole. In this regard, inclusion of a semi-rigid pole may resist over-flexing of the insertion tube due to the bias toward the installation configuration (e.g., straight or unbent) of the elongate member.

In another aspect, an apparatus for transporting a medical probe may comprise an elongate member, as described above, without a housing for the body of a medical probe. In this regard, a transport apparatus may include an elongate member comprising a biasing component, first and second fastening mechanisms attached to the elongate member, and an insertion tube retainer. A sanitary sleeve dispenser may also be optionally provided.

In another aspect, a system may include a transport apparatus as described herein and a medical probe, the medical probe comprising an ultrasound transducer configured for partial insertion into the esophagus of a patient. The medical probe may be disposed in the transport apparatus.

In yet another aspect, a method for use in transporting an ultrasound transducer may include inserting a body of the ultrasound transducer into a volume of space in a housing of a transport apparatus and closing the housing to substantially envelop the body of the ultrasound transducer within the housing. The closing the housing may comprise flexing an elastic material comprising a hinge connecting a lid portion of the housing to a base portion of the housing to rotationally pivot the lid portion with respect to the base portion. The method may further include securing, to an elongate member extending from the housing, an insertion tube extending from the body of the ultrasound transducer, the elongate member being in an installation configuration during the securing. The securing may include manipulating a portion of a first hook and loop fastener tab extending from the elongate member over the insertion tube such that the insertion tube is disposed between a portion of the first hook and loop fastener and the elongate member and manipulating a portion of a second hook and loop fastener tab into locking engagement with the first hook and loop fastener tab. Furthermore, the method may include manipulating the elongate member and insertion tube into an arch-shape, the elongate member and insertion tube being in a transport configuration while being in the arch-shape.

In an embodiment, the method may include inserting at least a portion of the insertion tube into a sanitary sleeve. The inserting may include removing the sanitary sleeve from a plurality of sanitary sleeves and inserting the insertion tube into the removed sanitary sleeve. The plurality of sanitary sleeves may comprise a roll of sanitary sleeves and the removing may include unrolling the sanitary sleeve from the roll.

In an embodiment, the method may include securing the elongate member to the housing to maintain the arch-shape of the elongate member and insertion tube.

In another embodiment, the method may include securing the elongate member to the housing. The securing may include engaging a first fastening mechanism attached to the elongate member with a second fastening mechanism attached to the housing.

In a further embodiment, the method may include inserting a portion of the insertion tube into a window through a portion of the housing. The insertion may occur prior to the closing the housing. The window may be at least partially aligned with a longitudinal centerline of the elongate member.

In another embodiment, the method may include transporting the transport apparatus from a first location to a second location, opening the housing, and removing the ultrasound transducer. Thereafter, the method may optionally include inserting a body of a second ultrasound transducer into the volume of space in the housing of the transport apparatus. The method may further include sanitizing the transport apparatus before the inserting of the body of the second ultrasound transducer.

In another aspect, a method for use in transporting an ultrasound transducer may include inserting a body of the ultrasound transducer into a volume of space in a housing of a transport apparatus, closing the housing to substantially envelop the body of the ultrasound transducer within the housing, manipulating the insertion tube into an arch-shape, the insertion tube being in a transport configuration while being in the arch-shape, and securing a distal end of the insertion tube relative to the housing to maintain the arch-shape. In this regard, a method of transporting an ultrasound transducer may not require the use of an elongate member but rather may rely upon securing an ultrasound to a housing.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended

DETAILED DESCRIPTION

Disclosed herein are utilities (e.g., methods, systems, and apparatuses) for protecting and transporting medical probes (e.g., ultrasonic transducers). Among other advantages, the disclosed utilities provide a sterility barrier to prevent environmental pathogens from contaminating a sterile medical probe and pathogens from a used medical probe from contaminating its surroundings during transport of the probe, limit physical damage to the probe during transport, and the like. While much of the description below makes use of specific examples in discussing various embodiments of the invention, such examples are intended merely for illustrative purposes and the invention is not necessarily to be limited by any operational characteristics disclosed herein.

Figure 1A:
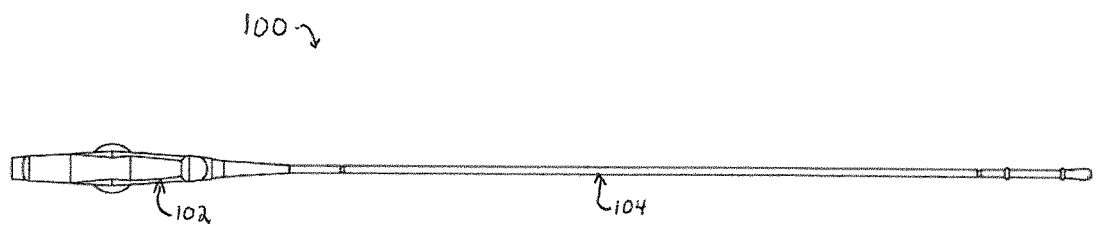
FIG. 1A is a bottom view of a medical probe as may be used in conjunction with a transport apparatus of the present invention.
Figure 1B:
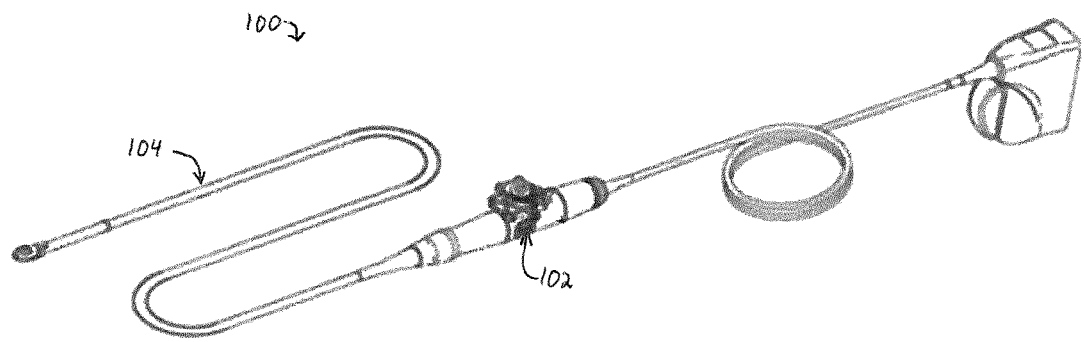
FIG. 1B is a perspective view of the medical probe of FIG. 1A having a cable attached.

Before discussing the disclosed utilities in more detail, reference will be made to FIGS. 1A and 1B which illustrate one representative medical probe which may be transported in conjunction with the present invention. The illustrated embodiment, although not intended to be limiting, is an ultrasound transducer, specifically a TEE probe 100 having a body 102 and an insertion tube 104. The body 102 may comprise a control housing configured to house various electrical components of the TEE probe 100. The insertion tube 104 may comprise a flexible material configured for insertion into a patient's mouth, esophagus, etc.

Figure 2:
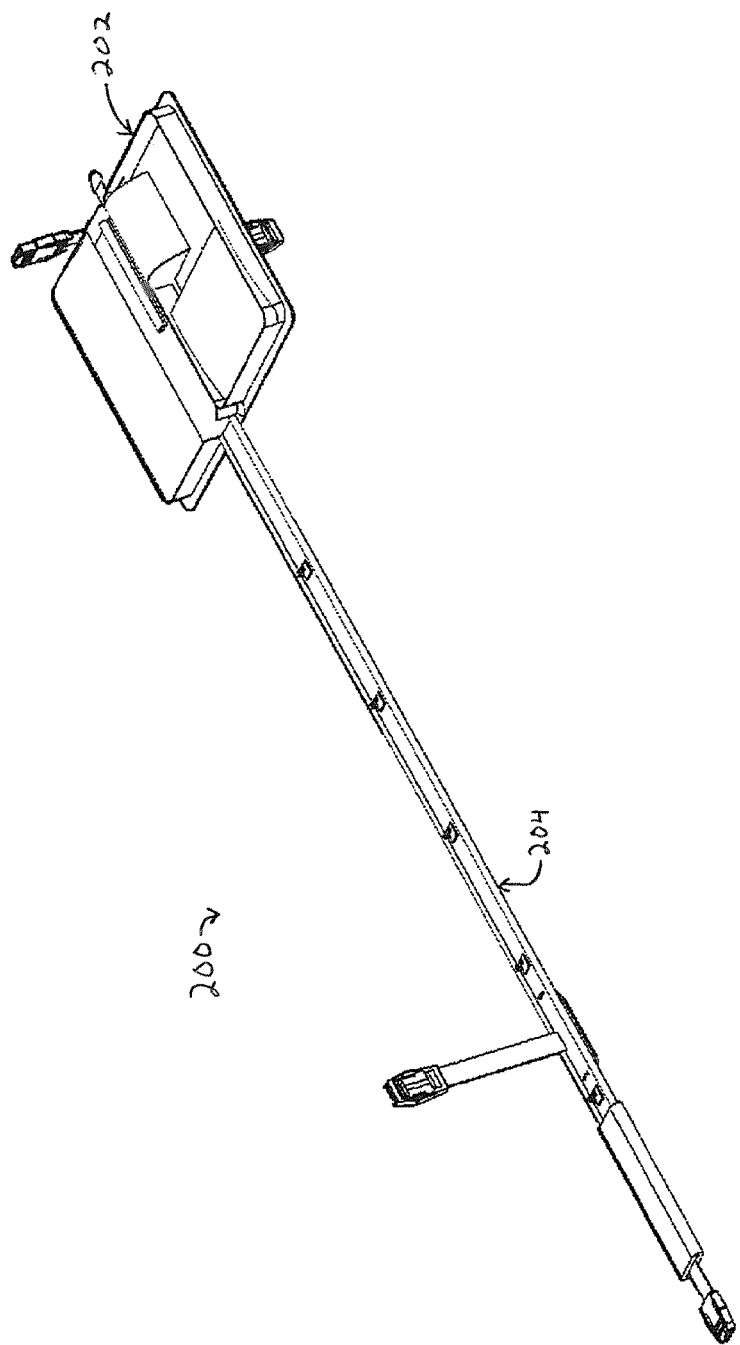
FIG. 2 is a perspective view of a medical probe transport apparatus according to one embodiment, with a housing apparatus being in an open configuration.
Figure 3:
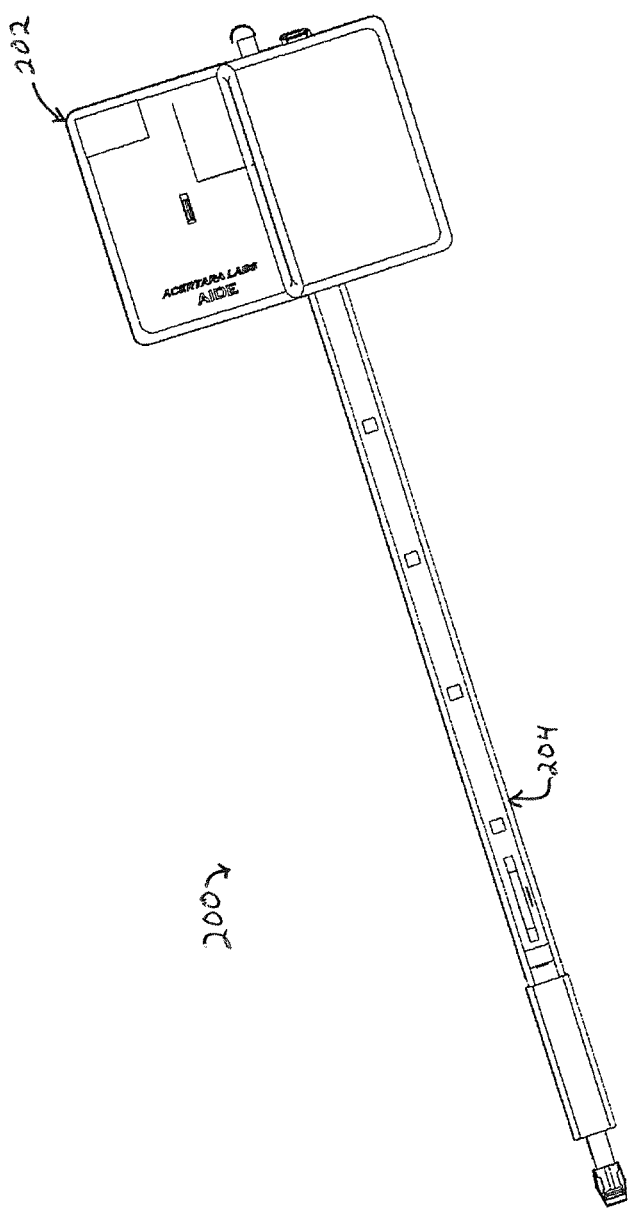
FIG. 3 is bottom view of the transport apparatus of FIG. 2.

With reference to FIGS. 2 and 3, a medical probe transport apparatus 200 is shown. The transport apparatus 200 generally comprises a housing 202 and an elongate member 204. The housing 202 is configured for receipt of a body of a medical probe. The body of a medical probe may comprise any portion of a medical probe for which it may be desirable to provide protection (e.g., a control housing of an ultrasound transducer). In this regard, protection provided by housing 202 may include a barrier from liquids which could damage electrical components, a barrier from pathogens or other contaminates, and a shield from impacts which might otherwise damage the body of the medical probe. An elongate member 204 is provided to accommodate the insertion tube which may not practically fit in the housing.

Elongate member 204 may be configured for receipt of the insertion tube of a medical probe and to retain the insertion tube in a desired configuration and orientation. In this regard, the elongate member 204 may have an installation configuration, as shown in FIG. 2, in which the elongate member 204 is substantially flat or linear thereby promoting ease of installation of the insertion tube, and also a transport configuration (as in FIG. 9) in which the elongate member 204 is curved into an arc (e.g., arch) shape with the insertion tube engaged therewith. In this regard, the overall length of the transport apparatus 200 may be reduced for ease of use. The elongate member 204 may be biased toward the installation configuration to aid in preventing the insertion tube from being over-flexed (such biasing being discussed in more detail below). The transport configuration may also secure the insertion tube to prevent it from flopping around or being mishandled in a manner that might cause damage. The elongate member 204 may comprise any suitable material such as a woven webbing or fabric strap, rubber, plastic, polymer, nylon, Kevlar®, and/or a similar material.

FIGS. 2 and 3 illustrate the transport apparatus 200 in a configuration in which the housing 202 is open. This open configuration may facilitate installation and removal of a medical probe, and specifically the body of the medical probe, into and out of the housing 202.

Figure 4:
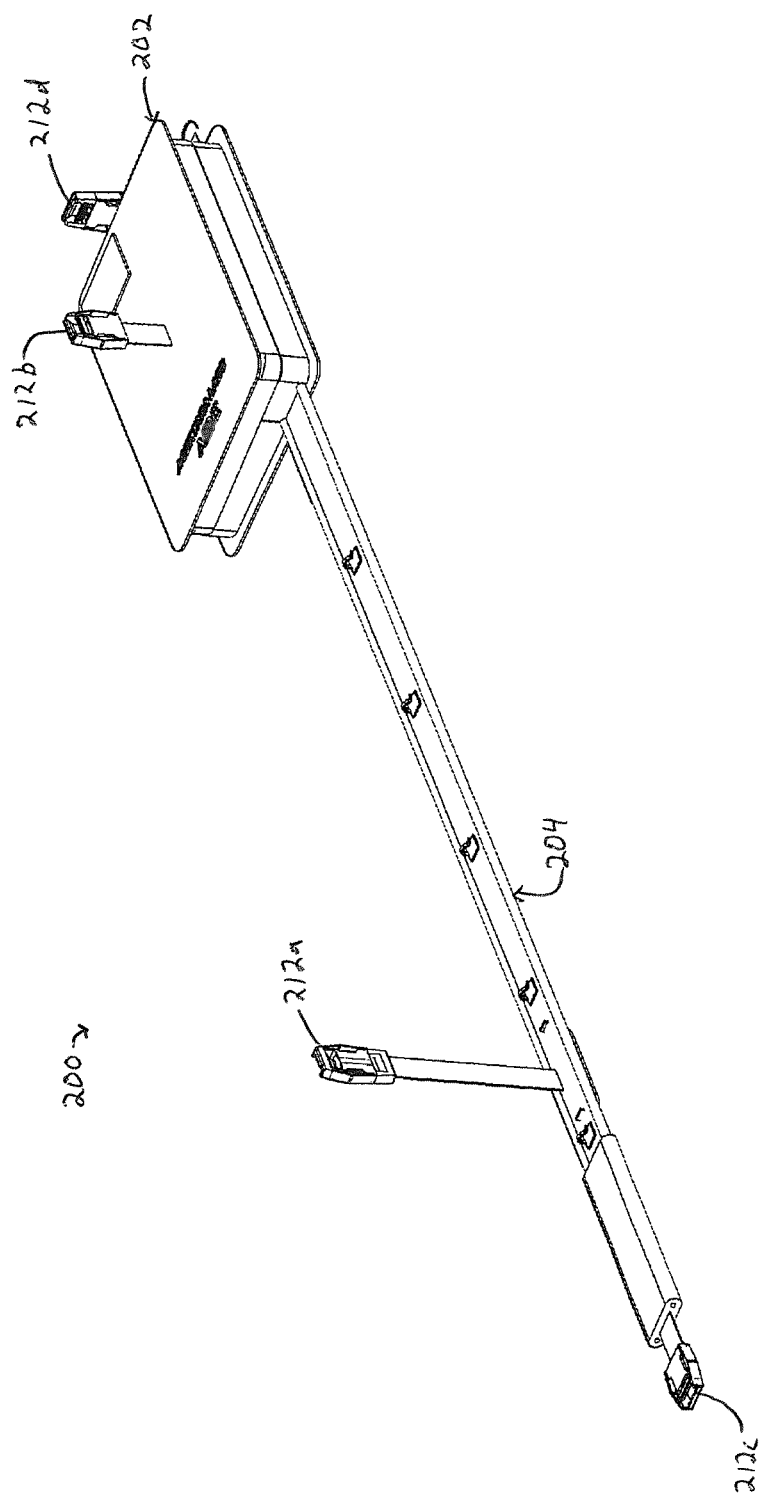
FIG. 4 is another perspective view of the transport apparatus of FIG. 2 with the housing being in a closed configuration.

FIG. 4 illustrates a transport apparatus 200 in a configuration in which the housing 202 is closed. This closed configuration may provide protection for the body of a medical probe during storage or transport. The housing 202 may be configured for transition between the open and closed configurations by any appropriate means. For example, a living hinge may be integrated into a portion of the housing 202 to facilitate flexural movement. Alternatively, a mechanical hinge may be disposed between two distinct portions of the housing 202 such as a base portion and a movable portion. In still other embodiments, a movable portion may be completely removable from a base portion (i.e., without a hinge).

FIG. 3 further illustrates fastening mechanisms which may be used to retain the elongate member 204 in a transport configuration. Fastening mechanisms may comprise any appropriate means for securing a portion of the elongate member 204 to a portion of housing 202 when the elongate member 204 is in a desired transport configuration. For example a pocket may be disposed on the housing 202 and configured for receipt of the tip of the elongate member 204. Alternatively, a hook fastener may be disposed near the tip of the elongate member 204 and a corresponding loop fastener may be disposed on the housing 202. In the illustrated embodiment, the fastening mechanisms used are snap latches 212 attached to the elongate member 204 and housing 202. For example, a first snap latch 212a may be configured for engagement (e.g., interconnection) with a second snap latch 212b. Similarly, a third snap latch 212c may be configured for engagement with a fourth snap latch 212d. Both pairs of snap latches 212 may be utilized simultaneously or only one pair of snap latches 212 may be utilized. In this regard, a first pair of snap latches may be configured to retain the elongate member 204 in a first radius of curvature and a second pair of snap latches may be configured to retain the elongate member 204 in a second radius of curvature. Such a plurality of configurations may permit a user to select a desired radius of curvature based upon characteristics of a medical probe. Notable, the snap latches 212 may be attached directly to the elongate member 204 or housing 202 or may be connected thereto via a webbing or a strap which is in turn attached to the respective part.

In another embodiment, a ratchet mechanism may be used in addition to or in lieu of snap latches 212. In this regard, a strap may be attached to either the housing 202 or the elongate member 204 and a corresponding ratchet may be attached to the other of the housing 202 or the elongate member 204. In this regard, a free end of the strap may be fed through and engaged with the ratchet to facilitate drawing a portion of the strap toward the ratchet, thereby cranking the elongate member 204 into a desired transport configuration.

Figure 5:
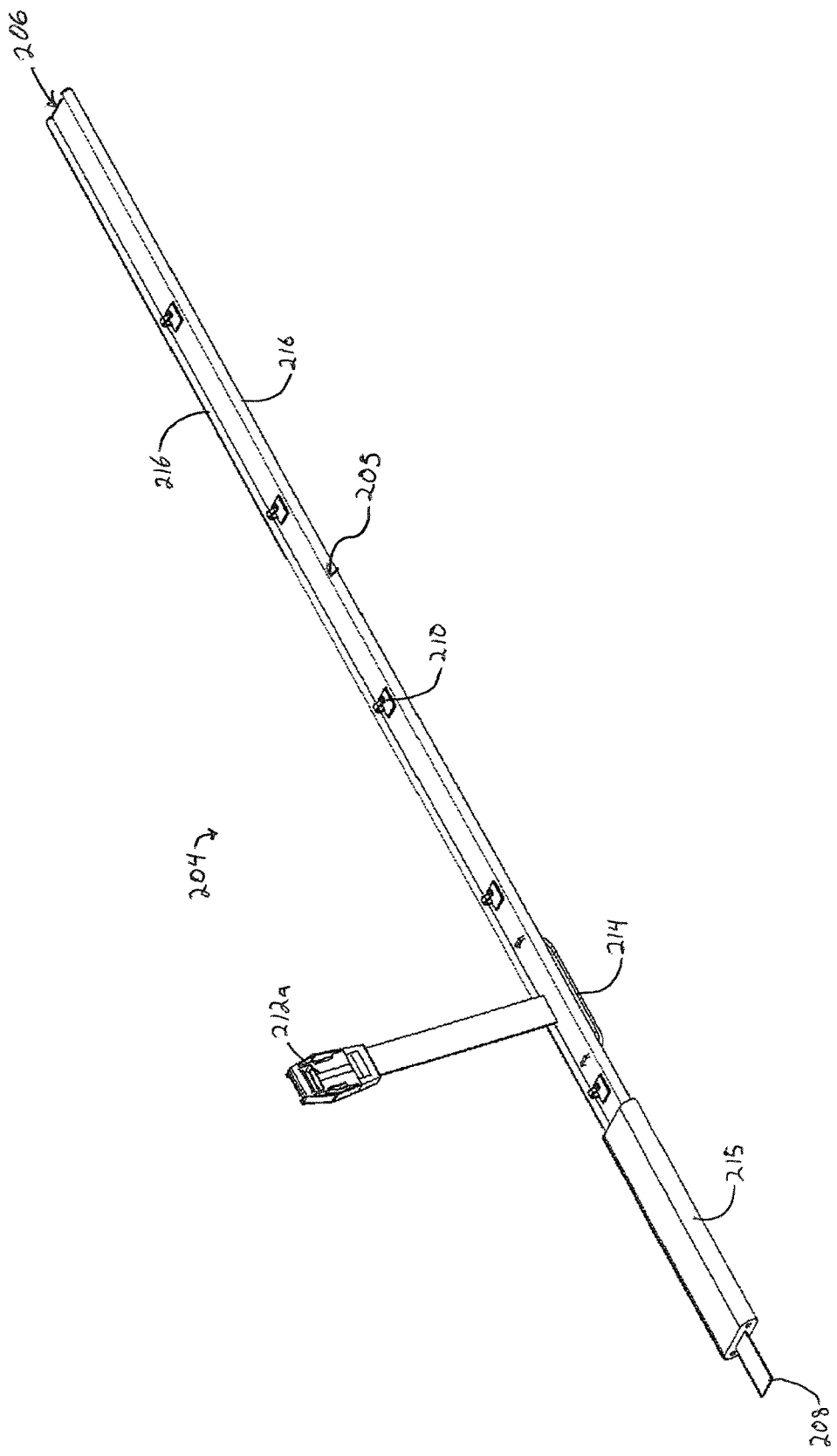
FIG. 5 is a perspective view of an elongate member of the transport apparatus of FIG. 2.

FIG. 5 illustrates an elongate member 204 of the transport apparatus 200. The elongate member 204 broadly includes a body 205 having a proximal end 206 that may be attached to a housing, and a distal end 208 opposite the proximal end 206 along an axis. Elongate member 204 may have an insertion tube retainer 210 attached to or formed as a part of the body 205. For instance, the insertion tube retainer 210 may be any device or plurality of devices configured to retain an insertion tube within the width of the elongate member 204 (e.g., in a direction transverse to the axis) during storage and transport. The insertion tube retainer 210 may include a plurality of clips disposed along the length of the elongate member 204. Each clip may be sized for receipt of an insertion tube. The insertion tube retainer 210 may be any device or plurality of devices configured to retain an insertion tube within the width of the elongate member 204 (e.g., in a direction transverse to the axis) during storage and transport. In other arrangements, the insertion tube retainer 210 may include hook and loop fasteners, pouches, a pocket disposed on the elongate member 204, and/or the like. Additionally or alternatively, a series of fabric strips oriented transverse to the axis may be sewn or bonded to the elongate member to form a plurality of orifices through which an insertion tube may be inserted (e.g., similar to belt loops).

The elongate member 204 may also include or incorporate a biasing component configured to bias the elongate member 204 toward the installation configuration (e.g., as shown in FIGS. 2-5) and resist bending. A biasing component may be a distinct device or may be integral with the elongate member 204. For example, a biasing component may comprise an inherent property of a material used to create the body 205 of the elongate member 204 (e.g., plastic), a semi-rigid material woven into fibers of the body 205 of the elongate member 204, or one or more semi-rigid poles attached to the body 205 of the elongate member 204. As used herein, semi-rigid may refer to a material property giving the biasing component a tendency to retain the elongate member 204 in the installation configuration while also being flexible enough to permit a user to bend the elongate member 204 into an arch. In this regard, the elongate member 204 may provide a tendency to bow out into an arch rather than simply fold in half as may be the case in the absence of a biasing component. In this regard, the bowed or arched shape, in conjunction with the insertion tube retainer, may hold the insertion tube in a similarly arched configuration. The tendency of the elongate member 204 to hold the insertion tube in a bowed, arched configuration may prevent or at least inhibit the insertion tube from being over-flexed into a radius of curvature smaller than that of the elongate member 204. In the illustrated embodiment, the biasing component comprises semi-rigid poles (not shown) disposed in compartments 216 sized to receive the poles and oriented parallel to the axis. In the illustrated embodiment, two poles and compartments 216 are used although it is envisaged that any number of poles could be used, for example, one pole in one compartment or four poles in one or more compartments. A compartment 216 may comprise a pouch, sleeve, or pocket formed on the elongate member 204. For example, a segment of fabric comprising the elongate member 204 may be folded and sewn to create a tubular pouch configured for receipt of one or more poles. Alternatively, a series of clips, straps, or other retainers may be used to secure the poles to the elongate member 204 in lieu of compartments 216.

An end cap 215 may be disposed at or near the distal end 208 of elongate member 204. For instance, an end of each semi-rigid pole may be disposed within a cavity of the end cap 215. End cap 215 may be comprised of a relatively hard material such as a hard plastic and may be rigidly attached to the elongate member 204. In this regard, end cap 215 may contain the ends of the semi-rigid poles and limit them from extending beyond the distal end 208.

Figure 9:
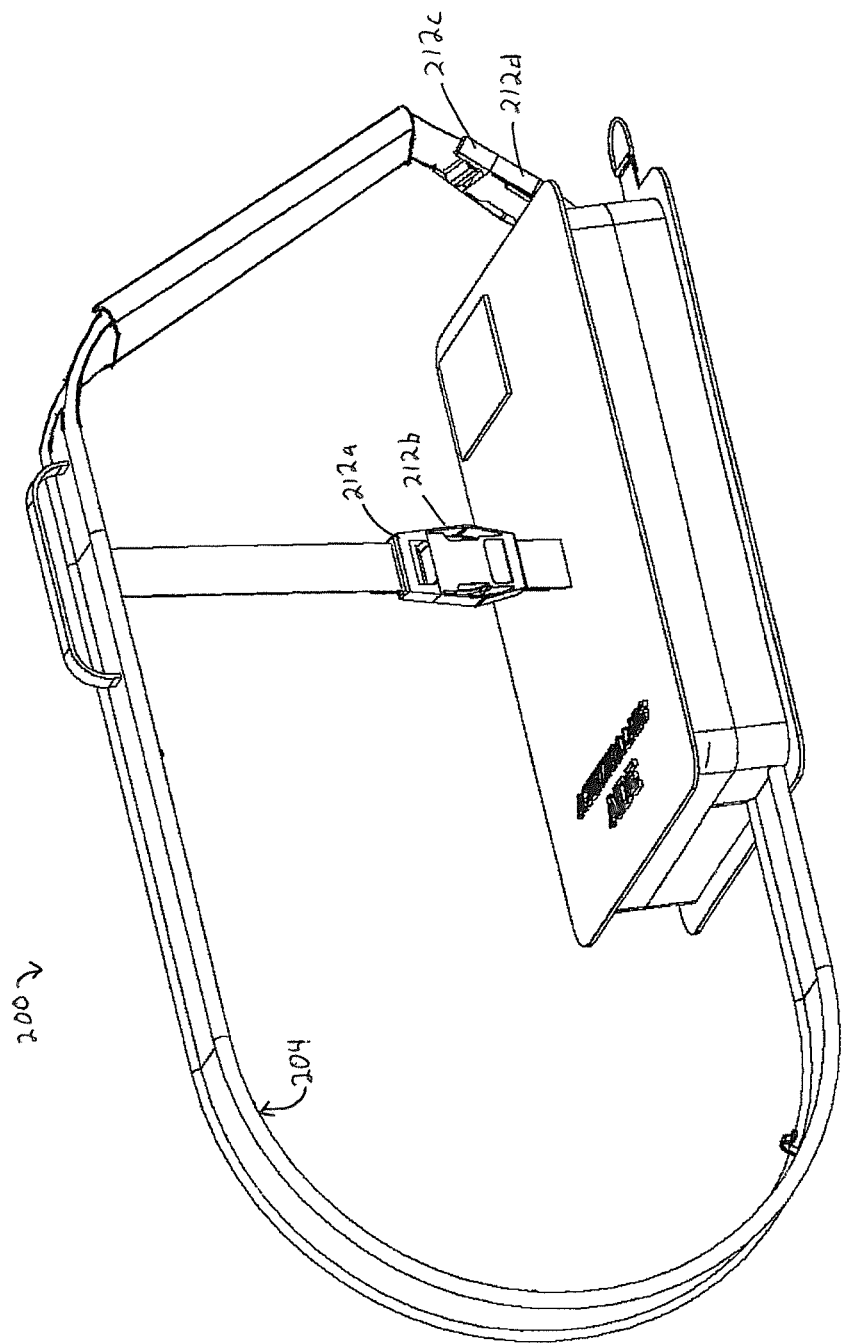
FIG. 9 is a perspective view of the transport apparatus of FIG. 2 in a transport configuration

In one arrangement, elongate member 204 may include a handle 214. For example, the handle 214 may be disposed on a side of the body 205 opposite the insertion tube retainer 210. In this regard, when the transport apparatus 200 is in the transport configuration (e.g., housing closed and elongate member bent and secured in relation to the housing, as shown in FIG. 9), the insertion tube may be disposed on the inside of the arched elongate member 204 while the handle remains accessible to a user on the outside of the arched elongate member 204. It should be appreciated that the handle 214 may be disposed in any location on the elongate member 204 or housing 202 to facilitate handheld transport of the apparatus 200.

Figure 6:
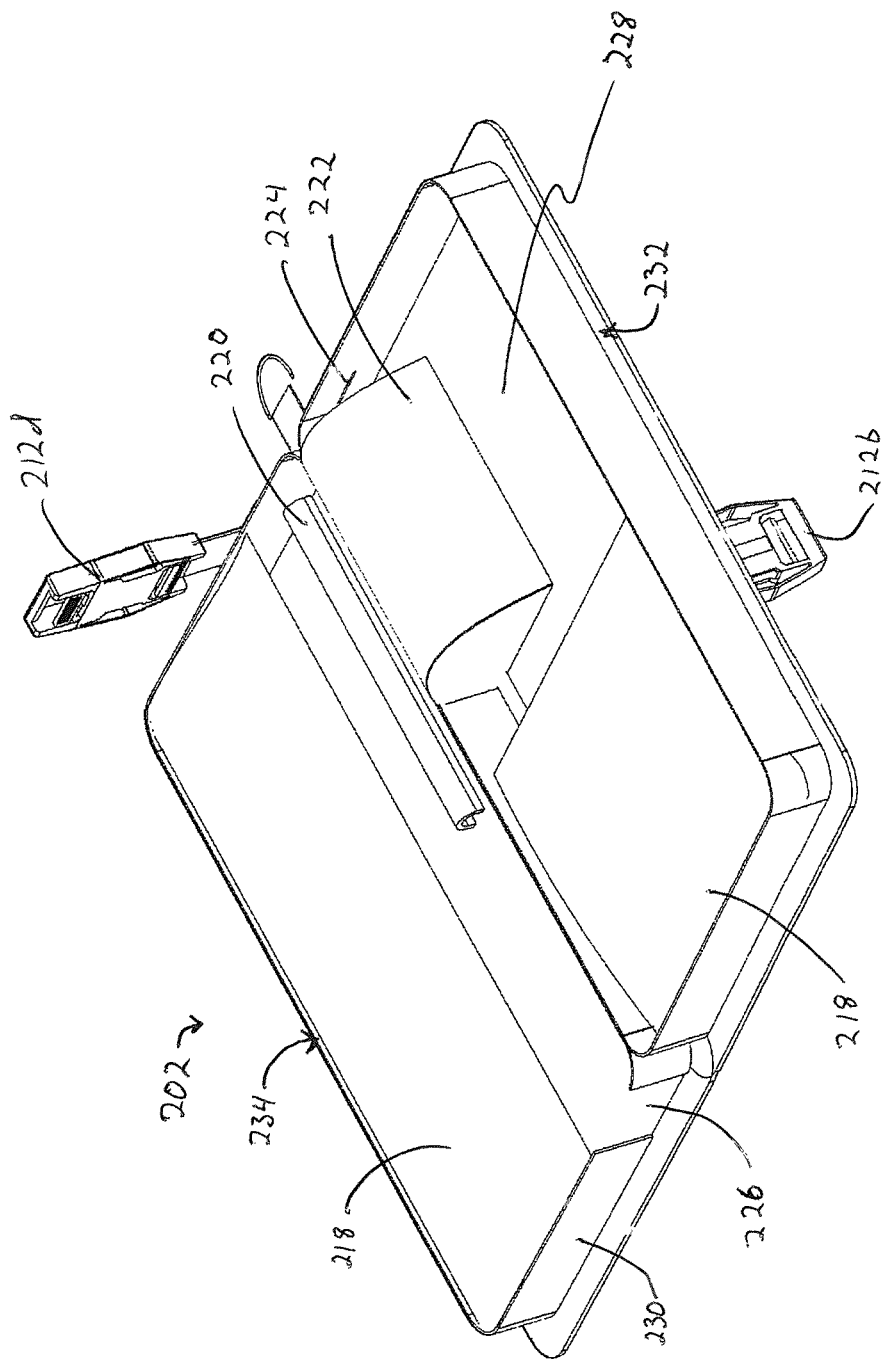
FIG. 6 is a perspective view of the housing of the transport apparatus of FIG. 2 being in the open configuration.
Figure 7:
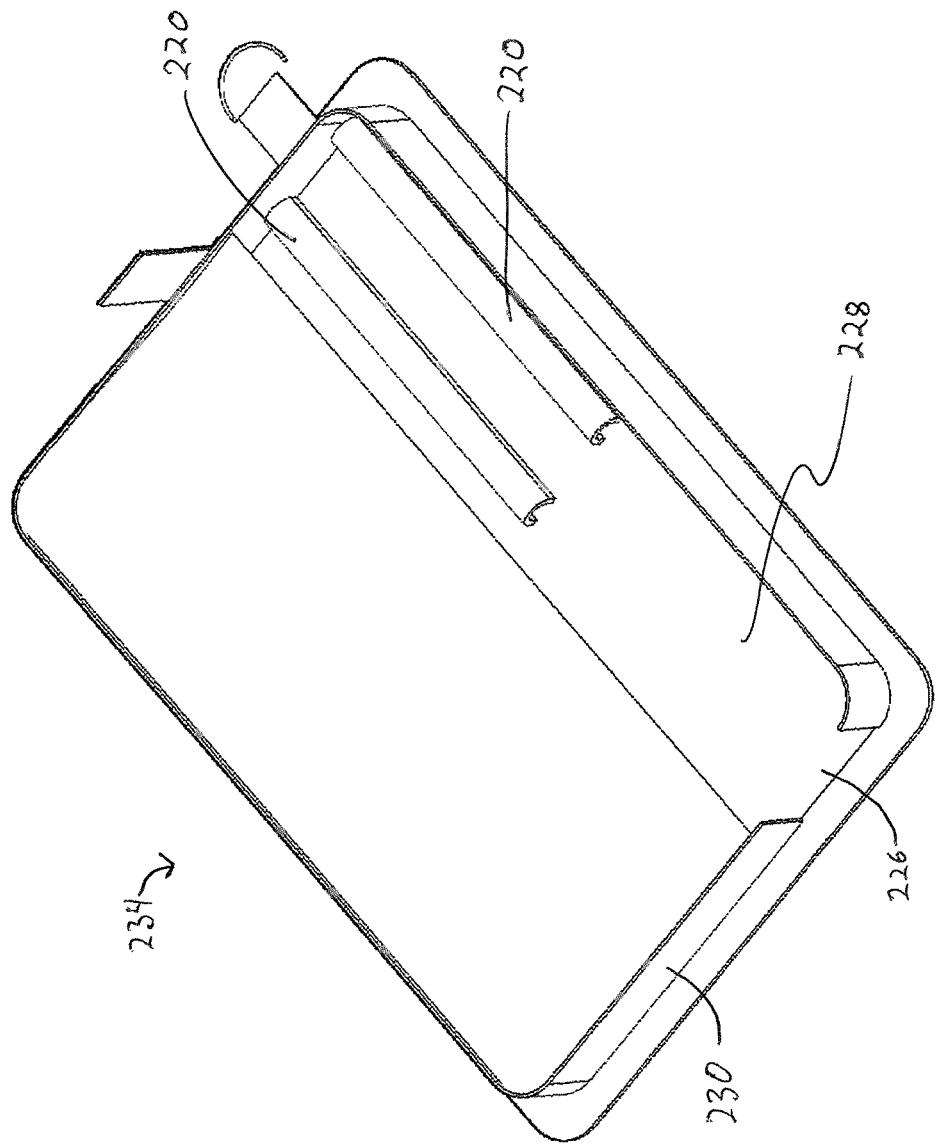
FIG. 7 is a perspective view of a base portion of the housing of the transport apparatus of FIG. 2.
Figure 8:
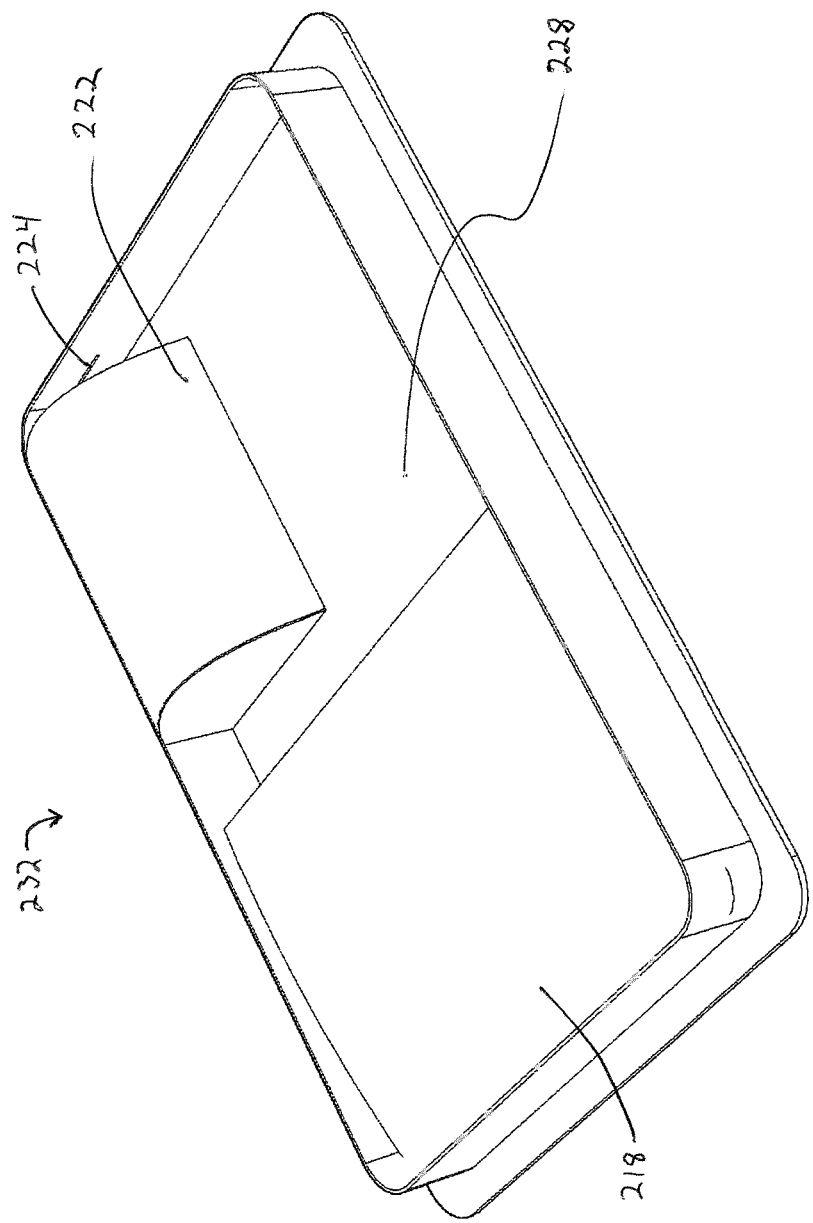
FIG. 8 is a perspective view of a movable portion of the housing of the transport apparatus of FIG. 2.

FIGS. 6-8 illustrate the housing 202 as having a base portion 234 and a movable portion 232 in an open configuration. In one arrangement, the movable portion 232 may be configured to pivot with respect to the base portion 234 to transition the housing 202 between the open configuration and closed configuration. For instance, a hinge may be provided between the base portion 234 and movable portion 232 to facilitate such pivotal relationship. The hinge may comprise a flexible material such as rubber or fabric (e.g., a living hinge) or may be a rigid mechanical hinge. Alternatively, a movable portion 232 may not be attached to base portion 234 by a hinge but rather may be configured to slide with respect to a slot or lip on the base portion 232, snap onto the base portion 232, or otherwise detachably engage the base portion 232.

An outer shell and/or walls of the housing 202 may comprise a rigid or semi-rigid material. For example, plastic, metal (e.g., aluminum, steel), rubber, carbon, or any other material sufficient to provide the functionalities of the housing 202 as described herein (e.g., impact protection, splash guard, etc.) may be utilized. The combination of the base portion 234 and movable portion 232 may define an internal cavity 228 that, when in the closed configuration, is sized for receipt of a body of a medical probe (e.g., body 102 of probe 100 of FIGS. 1A-1B). The internal cavity 228 may contain an insert 218 configured to cushion or protect the body. Such an insert 218 may include any suitable material such as, but not limited to, foam, plastic, or rubber. In the illustrated embodiment, the insert 218 includes a foam insert in the base portion 234 and a foam insert in the movable portion 232. These foam inserts may include a foam material with flexibility sufficient to conform to any shape of a body of a medical probe when the housing 202 is in the closed configuration. In other embodiments, an insert may comprise a cut-out (e.g., aperture or orifice) defining a volume sized and shaped to correspond to a body of a medical probe.

The housing 202 may include a plurality of walls (e.g., wall 230) defining a perimeter of the housing 202. In the illustrated embodiment, wall 230 includes a window 226 to facilitate receipt of a portion of a medical probe when the body of the medical probe is disposed within the housing 202. In this regard, a portion of the body, a portion of the insertion tube, or a portion of the medical probe connecting the body to the insertion tube may be at least partially disposed through the window 226 when medical probe is installed in the transport apparatus. In the illustrated embodiment, window 226 is disposed in a location in wall 230 that is aligned with the elongate member 204. In this regard, the insertion tube may extend from the elongate member 204 and into the housing 202.

A sanitary sleeve dispenser may be disposed on or within housing 202. In the illustrated embodiment, a sanitary sleeve dispenser 222 is disposed within the internal cavity 228 upon the movable portion 232. A roll of sanitary sleeves may be stored within the sanitary sleeve dispenser 222. A sanitary sleeve on the roll of sanitary sleeves may be at least partially extended through slot 224 to an exterior of the housing 202. In this regard, slot 224 may allow a user to remove a single sanitary sleeve from inside the housing 202.

In some embodiments, housing 202 may comprise a portion of the biasing component of the elongate member 204. For example, in the illustrated embodiment, semi-rigid poles engaged with the elongate member may extend into the housing 202 through window 226. An end portion of each semi-rigid pole may be disposed within one of the pole mounts 220. In this regard, the semi-rigid poles may be rigidly attached to the housing 202 to provide a leverage and/or anchor point when the semi-rigid poles are flexed. In conjunction with an end cap (e.g., end cap 215 of FIG. 5), the pole mounts 220 may serve to constrain the semi-rigid poles.

FIG. 9 illustrates the transport apparatus 200 in the transport configuration. In this configuration, fastening mechanism may retain the elongate member 204 in an arched-shape. For example, a snap latch 212a disposed on the elongate member 204 may be engaged with a corresponding snap latch 212b disposed on the housing 202. Similarly, snap latch 212c may be engaged with snap latch 212d. The biasing component of the elongate member 204 may exert an outward force tending to retain the elongate member 204 in a bowed (e.g., arched) shape.

Figure 10:
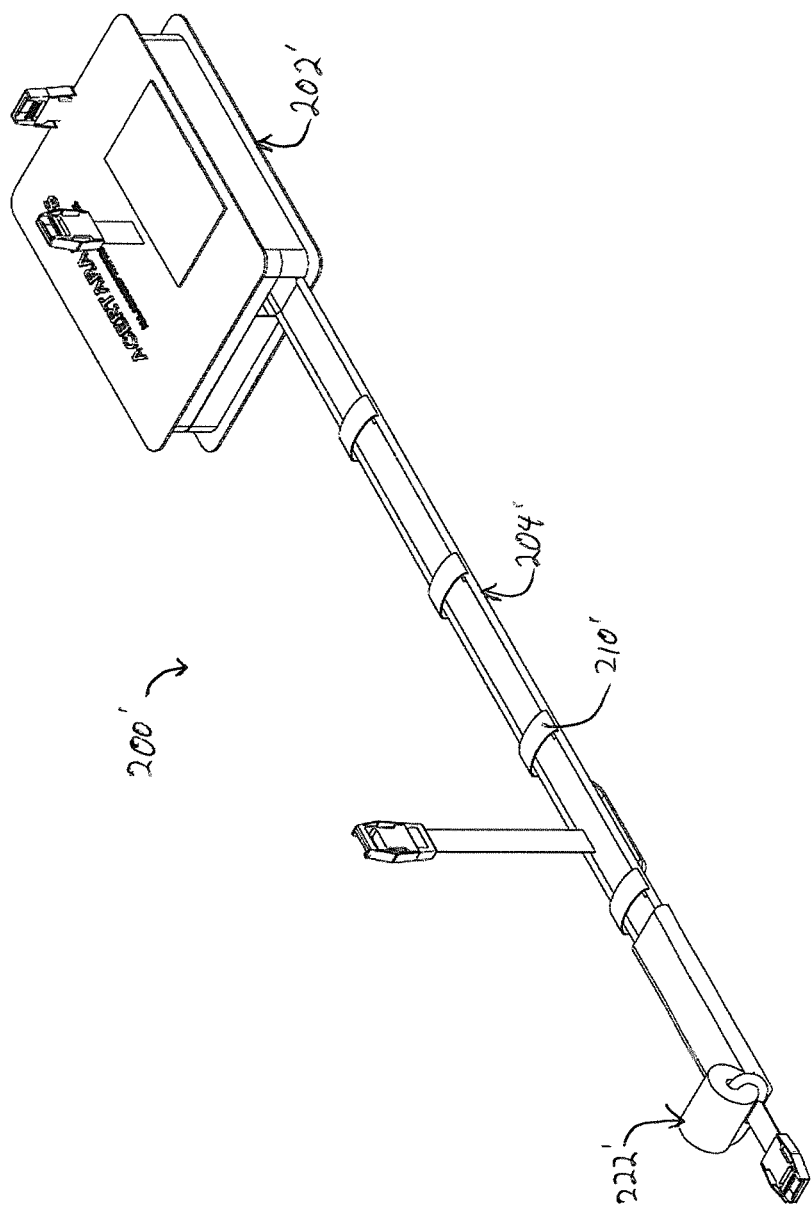
FIG. 10 is a perspective view of another embodiment of a transport apparatus.

FIG. 10 illustrates another embodiment of a transport apparatus 200' comprising a housing 202' and an elongate member 204' In the illustrated arrangement, the insertion tube retainer 210' comprises a plurality of hook and loop fasteners configured to engage over the top of an insertion tube when the insertion tube is disposed on the elongate member 204'. Sanitary sleeve dispenser 222' may be disposed near a distal end of the elongate member 204'. Sanitary sleeve dispenser 222' may house or hold a plurality of sanitary sleeves (e.g., plastic sleeves) sized to envelop at least a portion of an insertion tube and/or control housing to provide a sterility barrier between the medical probe and the transport apparatus 200' and thereby limit transfer of pathogens. In this regard, a sanitary sleeve may be disposed around the insertion tube prior to or during installation of the medical probe into the transport apparatus 200'.

Figure 11:
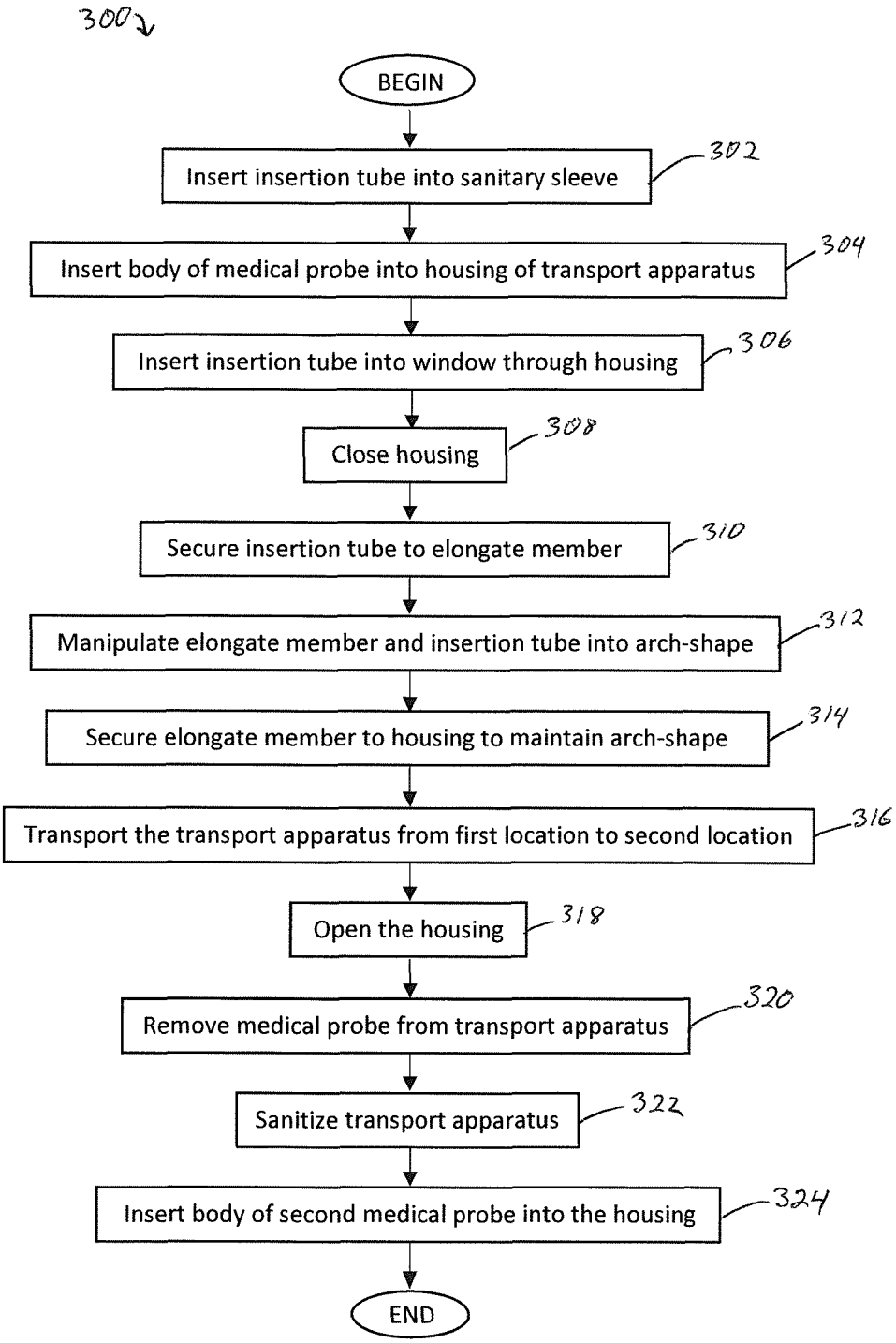
FIG. 11 is a flow chart of a method of transporting a medical probe.

FIG. 11 illustrates a method 300 for use in transporting a medical probe. The method may initiate with inserting 302 an insertion tube of a medical probe into a sanitary sleeve. The body of the medical probe may then be inserted 304 into the housing of a transport apparatus (e.g., with the housing 202 being in an open configuration as shown in FIGS. 2, 3, and 6). In one variation, the insertion tube may also be inserted into a sanitary sleeve after the body has been disposed within the housing. During step 304, the insertion tube may be inserted 306 into or otherwise disposed within a window of the housing. This may occur prior to, simultaneously with, or subsequent to inserting the body of the medical probe into the housing. With the body of the medical probe in the housing, the housing may be closed 308 (see, e.g., FIG. 4).

The method 300 may further comprise, securing 310 the insertion tube to the elongate member (e.g., with the elongate member 204 being in the installation configuration of FIGS. 2-5). The securing 310 may include affixing the insertion tube to the elongate member with one or more insertion tube retainers. Upon securing the insertion tube to the elongate member, the elongate member with the insertion tube may be manipulated 312 into an arch-shape (see, e.g., FIG. 9). The arch-shape may comprise a radius of curvature large enough to avoid damage from over-flexing the insertion tube. Once disposed in the arch-shaped configuration, the elongate member may be secured 314 to the housing to maintain the arch-shape. In this regard, the elongate member need not be secured or affixed directly to the housing but a fastening mechanism operatively attached to the elongate member may be interconnected to a corresponding fastening mechanism operatively attached to the housing.

The method 300 may further comprise transporting 316 the transport apparatus, with a medical probe installed therein, from a first location to a second location. In one arrangement, the first location may be an operating room where the medical probe is used and the second location may be a facility or laboratory designated for cleaning or sterilizing the medical probe. Upon arrival at the second location, the method may include opening 318 the housing and removing 320 the medical probe from the transport apparatus. Thereafter, the transport apparatus may be sanitized 322 to kill or remove any pathogens such that the body of a second medical probe may be safely inserted 324 into the housing.

Figure 12:
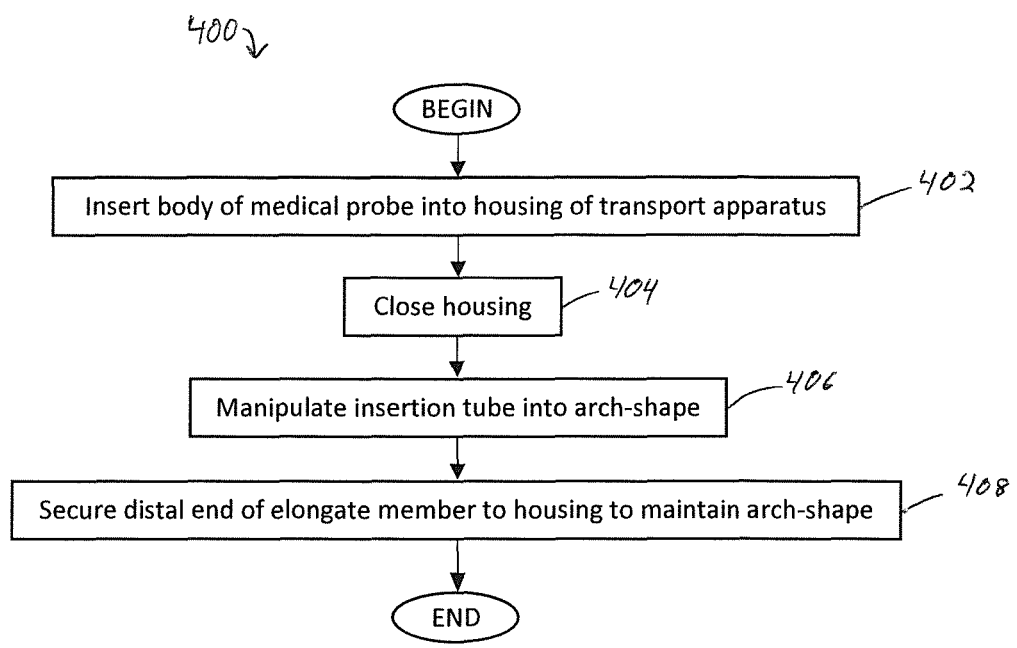
FIG. 12 is a flow chart of another method of transporting a medical probe.

FIG. 12 illustrates another embodiment of a method for use in transporting a medical probe 400, wherein an elongate member may not be utilized. The method 400 may initiate with a user inserting 402 a body of a medical probe into the housing of a transport apparatus, similar to step 304 of method 400. After insertion of the body of the medical probe, the method comprises closing 404 the housing around the body. Prior to or subsequent to closing the housing, the insertion tube may be manipulated 406 into an arch-shape. Once in the arch-shape, the user may secure 408 the distal end of the elongate member, opposite the body of the medical probe, to the housing to maintain the arch shape. The distal end of the elongate member may be secured in relation to the housing by any appropriate means including, but not limited to, inserting the distal end (e.g., tip) into a sleeve disposed on an exterior surface of the housing, inserting the distal end into a window of the housing, interconnecting two or more corresponding snap latches or other fastening mechanisms, etc.

Notably, the ordering of the steps in methods 300 and 400 of FIGS. 11 and 12 are shown for illustrative purposes only.

It is envisaged that steps may be reordered in any manner that facilitates the objectives described herein (e.g., protecting the body of the probe, arching the insertion tube, providing a sterility barrier, etc.). Additionally, some steps described may be optional.

Figure 13:
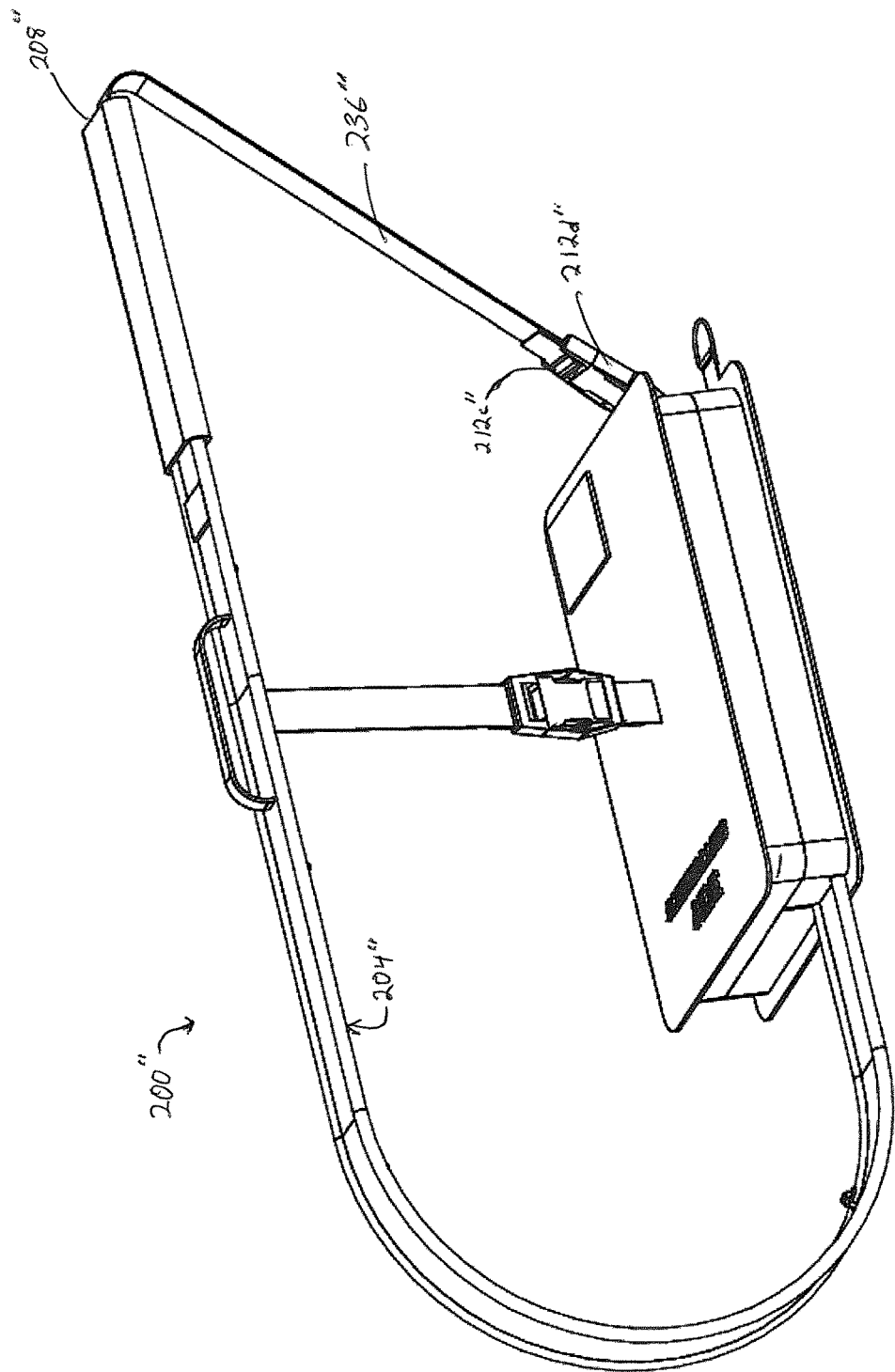
FIG. 13 is a perspective view of another embodiment of a transport apparatus in a transport configuration.

FIG. 13 illustrates another embodiment of a transport apparatus 200" in a transport configuration. In this embodiment, snap latch 212c" may be affixed to the elongate member 204" with an extended length of webbing or strap 236". In this regard, the strap 236" may allow the elongate member 204", and an insertion tube engaged therewith, to remain relatively linear near the distal end 208" to avoid unnecessarily over-flexing the insertion tube. The strap 236" may optionally be configured to mechanically extend and retract from within a portion of the elongate member 204". In this regard, the distal end 208" may be substantially constrained by the strap 236" and snap latches 212c", 212d" to prevent undesirable swinging of the insertion tube which may lead to damage, while also allowing a degree of flexibility to accommodate variations in insertion tube lengths, rigidities, etc. Further in this regard, a tensioning member may be provided to balance a force tending to retract the strap 236" with the force of the biasing component of the elongate member 204" to retain the insertion tube and elongate member 204" in a desired configuration.

While this specification contains many specifics, these should not be construed as limitations on the scope of the disclosure or of what may be claimed, but rather as descriptions of features specific to particular embodiments of the disclosure. Furthermore, certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

For example, in one arrangement, an elongate member 204 may be utilized alone without a housing (e.g., housing 202). In this regard, a medical probe may be disposed in an elongate member 204 as described herein such as when protection of a control housing is not required. A fastening mechanism may be configured to facilitate transport of the medical probe without a portion of the fastening mechanism disposed on a housing. For example, a snap latch may be disposed at or near the proximal end 206 of the elongate member 204 for engagement with snap latch 212a or a snap latch (not shown) may additionally or alternatively be disposed at the distal end 208. A plurality of snap latches 212 or other fastening mechanisms may be provided to present a user with various configuration options for selecting a radius or degree of curvature of the elongate member 204 and insertion tube when in use.

In other variations, a housing may include features different than those shown in housing 202. For example, a housing need not include a hard outer shell but may comprise a soft, impact-absorbing material (e.g., foam rubber) that is disposed around a body of a medical probe. Such a housing may be a spherical or ovate shape.

The above described embodiments including the preferred embodiment and the best mode of the invention known to the inventor at the time of filing are given by illustrative examples only.

What is claimed is:

1. An apparatus for transporting a medical probe, comprising:
   a housing configured for receipt of a body of the medical probe;
   an elongate member attached to the housing at a proximal end of the elongate member and extending away from said housing to a distal end opposite the proximal end, said elongate member having an installation configuration that is configured for receipt of an insertion tube of the medical probe, wherein the elongate member comprises a biasing component configured to bias the elongate member toward the installation configuration and resist bending of the elongate member;
   a first fastening mechanism attached to the elongate member; and
   a second fastening mechanism attached to the housing, wherein interconnection of the first and second fastening mechanisms maintains at least a portion of the elongate member in an arch-shape when the apparatus is in a transport configuration.

2. The apparatus of claim 1, further comprising:
   an insertion tube retainer attached to the elongate member and configured to restrict lateral movement of the insertion tube with respect to a width of the elongate member.

3. The apparatus of claim 2, wherein the insertion tube retainer comprises at least one hook fastener and at least one corresponding loop fastener extending from opposing sides of the elongate member.

4. The apparatus of claim 1, further comprising:
   a sanitary sleeve dispenser disposed on the apparatus and configured to dispense disposable sleeves, wherein the disposable sleeves are configured to envelop at least a portion of the insertion tube to form a sterility barrier between the insertion tube and the elongate member.

5. The apparatus of claim 4, wherein the sanitary sleeve dispenser is disposed adjacent the distal end of the elongate member upon a side of the elongate member configured for receipt of the insertion tube.

6. The apparatus of claim 4, wherein the sanitary sleeve dispenser is disposed on a portion of the housing.

7. The apparatus of claim 1, wherein:
   the housing comprises a movable portion to provide access to an internal cavity of the housing when the movable portion is in an open configuration;
   the internal cavity is sized for receipt of the body of the medical probe; and
   the body of the medical probe is at least partially enveloped within the housing when the movable portion is in a closed configuration.

8. The apparatus of claim 1, wherein the first fastening mechanism comprises a first snap latch disposed upon the housing and the second fastening mechanism comprises a corresponding second snap latch disposed adjacent to the distal end of the elongate member.

9. The apparatus of claim 1, wherein the housing comprises a foam insert defining a volume, said volume corresponding in shape to an electrical component control housing comprising the body of the medical probe.

10. The apparatus of claim 1, wherein the biasing component comprises semi-rigid fibers interwoven into fabric fibers of the elongate member.

11. The apparatus of claim 1, wherein the biasing component comprises the elongate member being comprised of a semi-rigid plastic material.

12. The apparatus of claim 1, wherein the biasing component comprises at least one semi-rigid pole configured for insertion into a compartment disposed on the elongate member.

13. The apparatus of claim 12, wherein the elongate member has a first radius of curvature when in the transport configuration without the at least one semi-rigid pole, and wherein the at least one semi-rigid pole comprises a resistance to bending sufficient to maintain the insertion tube in a second radius of curvature larger than the first radius of curvature when the apparatus is in the transport configuration with the at least one semi-rigid pole.

14. The apparatus of claim 1, further comprising:
a window comprising an opening through a portion of the housing, the window being configured for receipt of the insertion tube.

15. The apparatus of claim 14, wherein the window is aligned with the elongate member such that the insertion tube passes through the window when the medical probe is engaged with the apparatus in the transport configuration.

16. An apparatus for transporting a medical probe, comprising:
a housing configured for receipt of a body of the medical probe, wherein the housing comprises a movable portion to provide access to an internal cavity of the housing when the movable portion is in an open configuration, wherein the internal cavity is sized for receipt of the body of the medical probe, wherein the housing is configured to envelop the body of the medical probe when the movable portion is in a closed configuration, wherein a wall of the housing comprises a window through which an insertion tube of the medical probe is extendable outside the housing in the closed configuration; and
an elongate member that extends from a portion of the housing adjacent the window and configured for receipt of the insertion tube.

17. The apparatus of claim 16, wherein the housing comprises a foam insert defining a volume, said volume corresponding in shape to the housing.

18. An apparatus for transporting a medical probe, comprising:
an elongate member having a proximal end and a distal end opposite the proximal end, said elongate member having an installation configuration that is configured for receipt of an insertion tube of the medical probe, wherein the elongate member comprises a biasing component configured to bias the elongate member toward the installation configuration and resist bending of the elongate member;
a first fastening mechanism attached to the elongate member;
a second fastening mechanism attached to elongate member, wherein interconnection of the first and second fastening mechanisms maintains at least a portion of the elongate member in an arch-shape when the apparatus is in a transport configuration; and
an insertion tube retainer configured to restrict lateral movement of the insertion tube with respect to a width of the elongate member.

19. A system, comprising:
the apparatus of claim 18; and
the medical probe, the medical probe comprising an ultrasound transducer configured for partial insertion into the esophagus of a patient.

20. The system of claim 19, wherein the medical probe is disposed in the transport apparatus.

* * * * *